United States Patent [19]

Mimura et al.

[11] Patent Number: 4,543,238
[45] Date of Patent: Sep. 24, 1985

[54] SAMPLING APPARATUS

[75] Inventors: Tomonori Mimura; Hisayuki Sagusa; Takehide Satou; Katsuaki Takahashi, all of Katsuta, Japan

[73] Assignee: Hitachi, Ltd., Tokyo, Japan

[21] Appl. No.: 530,630

[22] Filed: Sep. 9, 1983

[30] Foreign Application Priority Data

Sep. 13, 1982 [JP] Japan .................. 57-158157

[51] Int. Cl.$^4$ .................. G01N 35/02; G01N 35/04
[52] U.S. Cl. .................. 422/63; 422/64; 422/65; 422/67; 73/863.24; 436/49
[58] Field of Search .................. 422/63–67, 422/100, 102; 73/863.24; 134/15, 34, 37; 436/49

[56] References Cited

U.S. PATENT DOCUMENTS

| | | | |
|---|---|---|---|
| 3,716,338 | 2/1973 | Moran | 422/65 |
| 4,076,503 | 2/1978 | Atwood et al. | 422/100 |
| 4,131,426 | 12/1978 | Range | 422/100 |
| 4,338,279 | 7/1982 | Orimo et al. | 422/65 |
| 4,343,766 | 8/1982 | Sisti et al. | 422/100 |
| 4,456,037 | 6/1984 | Gocho | 422/100 |

FOREIGN PATENT DOCUMENTS 55-69057  5/1980  Japan .................. 422/67

Primary Examiner—Michael S. Marcus
Attorney, Agent, or Firm—Antonelli, Terry & Wands

[57] ABSTRACT

A special cleaner is located between a sample cup at the sample absorbing position and a reaction case at the sample delivery position. This cleaner has a V-shaped recess, in which the cleaning liquid is filled in a pile. A pipetting tube is inserted into the sample cup, and a serum sample of the amount corresponding to a plurality of analysis items is absorbed and held by the pipetting tube. The pipetting tube hoisted upward is carried to the sample delivery position. In the process, the pipetting tube passes through cleaning liquid, so that the outer wall of the pipetting tube is cleaned within a short time, thus removing the excessive serum attached to the outer wall. The pipetting tube is lowered into the reaction case associated with the first analysis item to deliver a predetermined amount of serum sample thereinto. The pipetting tube is raised again and the train of reaction cases advances one step so that the tube is inserted into the next reaction case. After the delivery for a plurality of items, the inner and outer walls of the pipetting tube are cleaned.

6 Claims, 6 Drawing Figures

SAMPLING APPARATUS

BACKGROUND AND SUMMARY OF THE INVENTION

The present invention relates to a sampling apparatus and method, or more particularly to a sampling apparatus and method suitable for application to an automatic chemical analytical system of discrete action type.

In most of the conventional automatic chemical analytical systems, as disclosed in U.S. Pat. No. 4,298,570, a pipetting tube is cleaned only during the period after delivering the preceding sample into a reaction case before introducing another sample. The analytical system of single-line multi-analysis type, the use of which has recently been remarkably extended, also employs a similar cleaning operation.

In the case where one pipetting tube is used to perform the sampling operation for a plurality of analysis items in an ordinary analytical instrument, the pipetting tube is reciprocated between the sample absorbing position and the sample delivery position each time of introduction or absorption for an analysis item. The sampling of this method does not have high efficiency or speed in processing.

Accordingly, it is an object of the present invention to provide a sampling apparatus and method for an operation in such a manner that in the sampling operation from a sample cup to a reaction case by use of a pipetting tube, an accurate volume of a sample is distributed to a plurality of reaction cases with an increase of analysis items to be processed.

Another object of the present invention is to provide a sampling apparatus in which after introducing a volume of a sample designed for a plurality of analysis items into one pipetting tube at a time, sample portions of accurate amount are distributed sequentially to a plurality of reaction cases respectively.

According to an aspect of the present invention, there is provided a sampling apparatus comprising cleaning means including cleaning liquid exposed to contact the pipetting tube along the path thereof between the sample introducing position and the delivery position, so that the outer wall of the pipetting tube is cleaned by a layer of the cleaning liquid within a short time while passing through the cleaning means.

According to an embodiment of the present invention, even when a great amount of sample held in a pipetting tube is sequentially distributed to a plurality of reaction cases, the error in distribution amount is not increased, thus improving the sample-processing ability in practical applications. In fact, the sampling-processing rate is three times as high as that of the conventional systems. It has been found by the inventors that a serious problem is posed by the direct application of a new sampling method in which a sample is delivered in a plurality of parts after a single introduction thereof instead of in a single delivery following a single sample introduction as in the conventional methods. Specifically, the amount of the sample portion first delivered from the same pipetting tube is differentiated from that of the sample portions subsequently delivered therefrom. Experiments by the inventors show that the amount of the sample portion first delivered is always greater than that of the sample portions delivered for the second and subsequent times. This is found to be attributable to the fact that a small amount of the sample attaches to the outer wall of the pipetting tube. This problem has been obviated by the present invention.

In the case where a serum sample is introduced with the forward end of the pipetting tube dipped by 2 mm thereinto in a sample cup, the sample in the amount of approximately 0.1 µl attaches to the outer wall of the pipetting tube. When the outer wall is cleaned, on the other hand, the sample attached to the forward end of the pipetting tube is diffused into the cleaning liquid. The cleaning liquid, normally, pure water instead of the sample, is attached to the outer wall of the pipetting tube. The only effect of this water in a reaction case is to dilute the reagent reacting with the serum. If water in the amount of 0.1 µl is attached to the outer wall of the pipetting tube, for example, the reagent in the ordinary amount of 300 µl is diluted only by 0.03%, thus having substantially no effect on the analytical accuracy of the automatic analytical system.

The above and other objects, features and advantages will be apparent from the detailed description taken in conjunction with the accompanying drawings.

DETAILED DESCRIPTION

Figure 1:
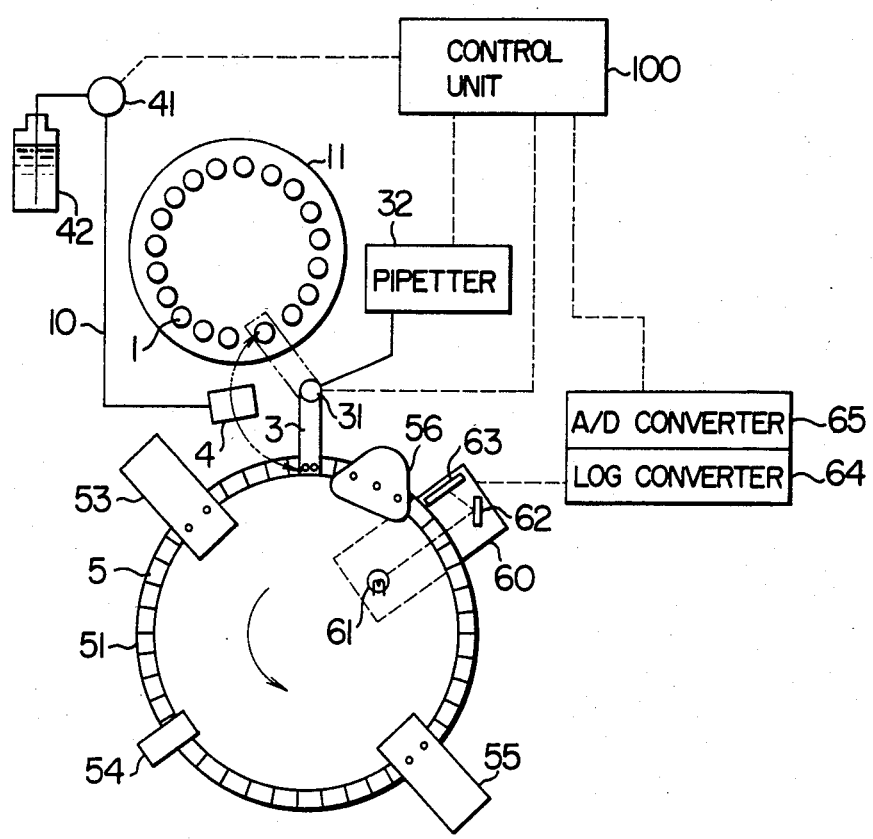
FIG. 1 is a diagram for explaining the general configuration of an example of the present invention applied to a biochemical automatic analytical system.

In FIG. 1, a sample disc 11 and a reaction table 51 are adapted to rotate intermittently. Sample cups 1 arranged on the sample disc 11 are sequentially set to a sample introduction position. A plurality of reaction cases 5 disposed on the reaction table 51 are also positioned at a sample delivery position sequentially. The reaction table 51 is provided, therearound, with a sampling mechanism 31, a first reagent supplier 53, an agitator 54, a second reagent supplier 55, a multi-wavelength spectrophotometer 60 and a reaction case cleaner 56. In the reaction cases, the sample reacts with the reagent, and the resulting liquid is measured optically by the multi-wavelength spectrophotometer 60. The reaction case or reaction cell 5 located in the light path is radiated with light from a light source 61, and the transmitted light is dispersed at a concave grating 62, so that a multiplicity of monochromatic light are received at a detector 63. The signal associated with one of the required analysis items is converted into a digital signal by an analog-digital converter 65 through a log converter 64, followed by the concentration calculation of the particular analysis item at a control unit 100.

The sampling mechanism 31 is adapted to rotate or vertically drive a sampling arm 3. A pair of pipetting tubes are suspended from the sampling arm 3 and communicate with the syringe mechanism in a pipetter 32. The pipetting tube cleaner 4 is connected through a cleaning water introduction tube 10 to a pump 41. This pump 41 supplies the cleaning water from a rinse water tank 42 to the cleaner 4 whenever required.

Figure 2:
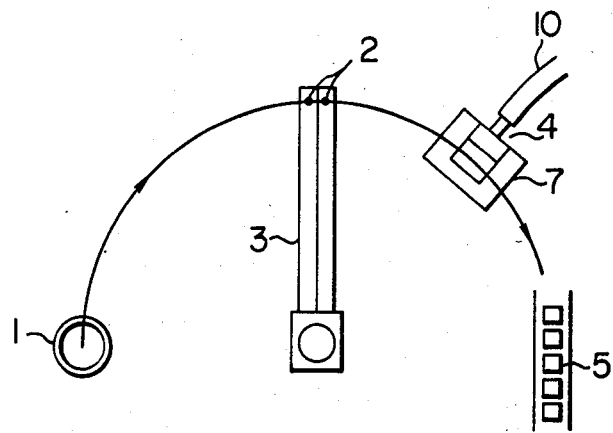
FIG. 2 is a plan view showing the path of the pipetting tube in the embodiment of FIG. 1.
Figure 3:
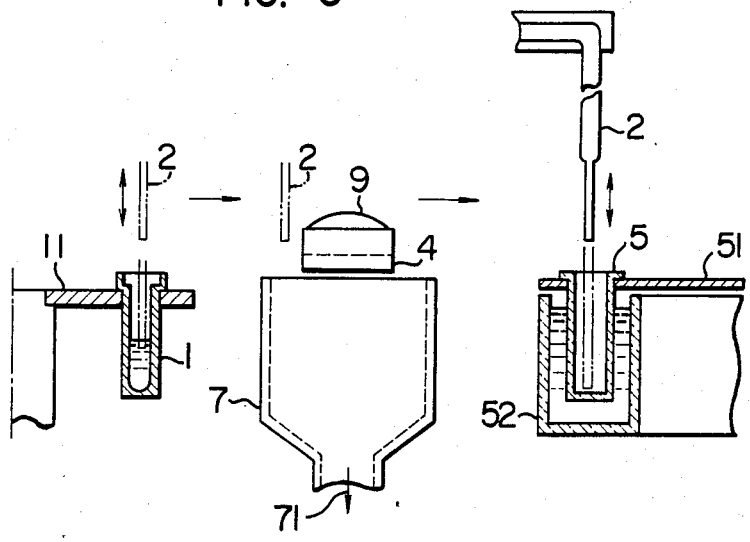
FIG. 3 is a diagram for explaining the vertical and lateral movements of the pipetting tube.
Figure 4:
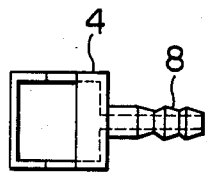
FIG. 4 is a plan view showing members of a cleaner according to an embodiment.
Figure 5:
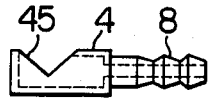
FIG. 5 is a side view of the members of FIG. 4.
Figure 6:
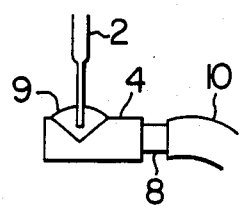
FIG. 6 is a diagram showing the manner in which the pipetting tube passes through the recess of the cleaner.

As seen from FIGS. 4 to 6, the cleaner or wash vessel 4 is connected with the cleaning water introduction pipe 10 by a connector 8. The cleaner 4 has a V-shaped opening 45 which is wider upward along the path of the pipetting tube 2. As shown in FIGS. 3 and 6, the pipetting tube 2 is passed through the inside of the V-shaped opening 45. While the pipetting tube 2 passes through the cleaner 4, the cleaning water is supplied to the opening 45 from the pump 41 to form a pile of cleaning water 9. It is seen from FIGS. 2 and 3 that a cleaning water receiver 7 is provided under the cleaner 4. The cleaning water, when supplied in great amount to the cleaner 4, overflows from the cleaner 4. This water overflow is received at the receiver 7 and is discharged through a drain 71. The operation of the sampling mechanism 31, the pipetter 22 and the pump 41 are controlled by the control unit 100.

In this embodiment, as shown in FIG. 3, the height of the sample cups 1 arranged on the sample disc 11 is substantially the same as that of the reaction cases 5 arranged on the reaction table 51 in a manner to be immersed in a constant-temperature bath 52. The upper side of the cleaner 4 is higher than the upper side of the sample cups 1 or the upper side of the reaction cases 5. At the sample introduction position, the pipetting tube 2 is lowered into the sample cup 1, and after absorbing and holding the serum sample, is raised. At the sample delivery position, on the other hand, the pipetting tube 2 is lowered into the reaction case 5, and after delivering the sample portion for one item, is raised. In other words, the pipetting tube 2 is moved vertically at the sample introduction position and delivery position, while the pipetting tube 2 is moved laterally in raised state at other positions. Under this condition, the forward end of the pipetting tube 2 is slightly higher than the root of the V-shaped opening 45 of the cleaner 4 and therefore the tube 2 crosses the cleaner 4 without contacting the cleaner 4.

Now, explanation will be made of a specific example of successive deliveries of the serum by a single pipetting tube. First, reference is made to an example of two successive deliveries.

With the pipetting tube 2 positioned above the sample cup 1, the syringe mechanism of the pipetter 32 is actuated to absorb the air in the amount of 15 μl. The pipetting tube 2 is then lowered and dipped into the serum in the sample cup 1 to absorb 5 μl of the dummy serum. The sample liquid surface is detected by a liquid level detector attached to the pipetting tube 2 so that the forward end of the pipetting tube 2 is prevented from being dipped more than 2 mm into the sample.

After absorbing a predetermined amount of the serum, for example, 10 μl for two items, the pipetting tube 2 is raised and while being maintained in raised state, is horizontally moved toward the reaction case 5 along an arcuate curve.

In the process of horizontal movement, the forward end of the pipetting tube 2 is maintained at the height about 2 mm lower than the upper side of the recess of the cleaner 4 while being passed through the pile of the cleaning liquid 9. As a result, the serum attached to the outer wall of the forward end of the tube 2 is removed. In this case, the pipetting tube 2 is maintained at proper depth and is prevented from being immersed in the cleaning water for an unnecessarily long time. If the pipetting tube 2 is immersed in the cleaning water unnecessarily deep or for an unnecessarily long time, the sample in the pipetting tube 2 is diluted by diffusion, thus causing a negative error in the first sampling. In other words, it is essential to clean the sample off from the outer wall of the pipetting tube effectively without diluting the sample in the pipetting tube 2.

Exactly at the time when the pipetting tube 2 passes along the V-shaped trough of the opening at the upper side of the cleaner 4, the deionized cleaning water is supplied through the cleaning water pipe 10 to form the water pile 9. As shown in FIGS. 3 and 6, the pipetting tube 2 passes through the surface portion of the water pile 9 to be cleaned. After passage of the pipetting tube 2, the cleaning water stops being delivered on the one hand and the cleaning water portion that has overflowed from the cleaner 4 is drained through the cleaning water receiver 7 on the other hand.

The pipetting tube 2, after passing through the cleaner 4, is transported to a point above the reaction cell 5, whereat the tube 2 is lowered to such a level that the forward end of the pipetting tube 2 comes into contact with the bottom of the reaction cell 5. Under this condition, the serum portion for one item is delivered. The serum thus delivered expands over the cell bottom and never attaches to the outer wall of the forward end of the tube 2. After delivering the first serum, the pipetting tube 2 is driven upward and the reaction table 51 is rotated, so that the tube 2 is inserted into the adjacent reaction cell 5. The serum is delivered for the second time in the same manner as in the first delivery. In this system, the result of measuring the total amount of protein contained in the serum (including the reproducibility and serum attachment) is shown in Table 1 below.

TABLE 1

|  | First serum delivery | Second serum delivery |
| --- | --- | --- |
| n | 30 | 30 |
| x | $\overline{X}_1 = 5.10$ (g/dl) | $\overline{X}_2 = 5.07$ (g/dl) |
| SD | 0.029 | 0.027 |
| CV | 0.57% | 0.53% |
| Serum attachment | Amount attached (%) = $(1 - \overline{X}_2/\overline{X}_1) \times 100 = 0.6$ | |

Note:
Control serum (monitrol II X) is used as a sample, and n designates the number of the delivery, x the average amount, SD the standard deviation and CV the coefficient of variation.

The reproducibility took the coefficient of variation of 0.5%. The error of the first delivery was also satisfactorily at 0.6%. Where the cleaning with water is not effected like in the preceding case, the difference between the amount of the first serum delivery and the second serum delivery for the delivery amount of 3 μl is more than 5%, while by cleaning the forward end of the pipetting tube 2, the difference is reduced to less than 1% for the serum delivery amount of 3 μl, or less than one fifth the difference otherwise caused by the sample attached to the outer wall of the forward end of the pipetting tube 2.

Apart from the two successive deliveries in a cycle as in the aforementioned case, four deliveries, for example, may be effected in succession in similar fashion. A number of successive deliveries save the time required for relocation of the pipetting tube, thus improving the processing speed of the samples.

Table 2 shows the result of measurements of the total protein contained in the serum in a sampling operation involving three serum deliveries in response to one serum introduction.

TABLE 2

|  | First serum delivery | Second serum delivery | Third serum delivery |
|---|---|---|---|
| n | 30 | 30 | 30 |
|  | $\overline{X}_1 = 5.09$ (g/dl) | $\overline{X}_2 = 5.07$ (g/dl) | $\overline{X}_3 = 5.06$ (g/dl) |
| SD | 0.031 | 0.026 | 0.027 |
| CV | 0.60% | 0.51% | 0.54% |
| Serum attachment | Amount attached (%) = $(1 - \overline{X}_2/\overline{X}_1) \times 100 = 0.4$ | | |
|  | Amount attached (%) = $(1 - \overline{X}_3/\overline{X}_1) \times 100 = 0.6$ | | |

Note:
Control serum (monitrol II X) is used as a sample.

Further assume that the serum for four analysis items is introduced into the pipetting tube at a time, and after passing this tube through the cleaning water, the serum is sequentially distributed into four reaction cases. In this case, too, the distribution error of the sample amount of the first delivery is small. Furthermore, four successive deliveries make possible a high delivery speed of 600 times per hour.

Unlike in the abovementioned embodiment comprising a single cleaner, a pair of cleaners may be provided: one for the purpose of cleaning the outer wall of the pipetting tube within a short time, with the sample held in the pipetting tube, the other for cleaning the inner and outer walls of the pipetting tube sufficiently in order to prevent mutual contamination of the samples after distribution of the sample to a plurality of reaction cases before the introduction of the next sample by the pipetting tube.

If these two functions are to be performed by a single cleaner, after distribution of a sample into reaction cases before the introduction of the next sample, the pipetting tube 2 is stopped at the position of the cleaner 4, the serum remaining in the tube is drained, the outer wall of the tube is cleaned in the arrangement shown FIG. 6 and the cleaning water is supplied through the forward end opening into the tube and discharged through the opening into the cleaning water receiver.

We claim:

1. A sampling apparatus comprising:
   sample container conveying means for conveying a plurality of sample containers,
   reaction container conveying means for conveying a plurality of reaction containers,
   pipetting tube means for transferring a sample from a sample container to a reaction container,
   wash vessel means situated in a pathway between said sample container conveying means and said reaction container conveying means and having cutouts formed in sidewalls thereof for passing said pipetting tube means across and through said wash vessel means, and
   control means for controlling the movement of said pipetting tube means and supplying cleaning liquid in said wash vessel means, wherein the lower end of said pipetting tube means extends vertically below the uppermost edge of a wall of said wash vessel means, and said control means moves said pipetting tube means through the wall of said wash vessel means by passing across said cutouts.

2. A sampling apparatus according to claim 1 wherein said control means controls said pipetting tube means to dispense sample into a reaction container.

3. A sampling apparatus according to claim 1 wherein said control means moves said pipetting tube means without pause during transferring of the sample from a sample container to a reaction container and so that after said transfer of said sample to a reaction container the pipetting means moves with a pause at said wash vessel means for cleaning of an inner wall of said pipetting tube means.

4. A sampling apparatus according to claim 1 wherein said control means moves said pipetting tube means so that an outer wall thereof is cleaned by passing said wash vessel means across said cutouts before the sample is dispensed in said reaction container, and so after dispensing said sample an inner wall of said pipetting tube means is cleaned by discharging cleaning liquid intaken therein.

5. A sampling apparatus according to claim 4 wherein said control means moves said pipetting tube means without pause during transferring of the sample from a sample container to a reaction container and so that after the transfer of sample to the reaction container the pipetting tube means is moved with pause at said wash vessel means to clean up an inner wall of said pipetting tube means.

6. A sampling apparatus comprising a sample absorbing station, a sample dispensing station and pipetting tube means for absorbing and holding a sample from a sample cup located at said sample absorbing station and dispensing at least part of the sample held into a reaction container located at said sample delivery station, means for moving said pipetting tube means along a path leading from said sample absorbing station to said sample dispensing station, and wash vessel means with exposed cleaning liquid located in a manner to contact said pipetting tube means as it is moved along said path by said means for moving, said wash vessel means having a pair of opposed side wall portions which are each formed with a cutout in an uppermost portion thereof and wherein said means for moving moves said pipetting tube means through said wash vessel means and the cleaning liquid therein by passing said pipetting tube means across and through said cutouts.

* * * * *